United States Patent
Simon et al.

[11] Patent Number: 6,074,809
[45] Date of Patent: Jun. 13, 2000

[54] COLOR PHOTOGRAPHIC SILVER HALIDE MATERIAL

[75] Inventors: Lydia Simon, Wülfrath; Günter Helling, Odenthal; Beate Weber, Leichlingen, all of Germany

[73] Assignee: Agfa-Gevaert N.V., Belgium

[21] Appl. No.: 09/208,233

[22] Filed: Dec. 9, 1998

[30] Foreign Application Priority Data

Dec. 16, 1997 [DE] Germany .................. 197 55 810

[51] Int. Cl.⁷ .............. G03C 1/08; G03C 7/26; G03C 7/32
[52] U.S. Cl. .............. 430/548; 430/543; 430/552; 430/553
[58] Field of Search .................. 430/543, 548, 430/552, 553

[56] References Cited

U.S. PATENT DOCUMENTS

| | | | |
|---|---|---|---|
| 3,767,412 | 10/1973 | Monbaliu et al. | 96/100 |
| 4,455,366 | 6/1984 | Hirano et al. | 430/548 |
| 4,495,272 | 1/1985 | Yagihara et al. | 430/548 |
| 4,496,650 | 1/1985 | Yagihara et al. | 430/548 |
| 4,511,647 | 4/1985 | Hirano et al. | 430/548 |
| 4,518,687 | 5/1985 | Hirano et al. | 430/548 |
| 4,804,620 | 2/1989 | Tang et al. | 430/548 |
| 4,921,782 | 5/1990 | Helling et al. | 430/548 |
| 4,946,771 | 8/1990 | Maekawa et al. | 430/548 |
| 5,141,844 | 8/1992 | Lau et al. | 430/548 |
| 5,151,356 | 9/1992 | Sakanoue et al. | 430/548 |
| 5,972,586 | 10/1999 | Mizukawa et al. | 430/548 |

FOREIGN PATENT DOCUMENTS 283 938  3/1988  European Pat. Off.
316 955  11/1988  European Pat. Off.

*Primary Examiner*—Geraldine Letscher
*Attorney, Agent, or Firm*—Connolly Bove Lodge & Hutz, LLP

[57] ABSTRACT

A color photographic silver halide material having a support, at least one photosensitive silver halide emulsion layer and a polymeric cyan coupler associated with the photosensitive silver halide emulsion layer, which coupler contains polymerised units of the formula (I)

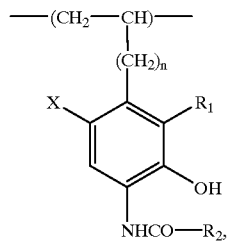

(I)

in which

X means a hydrogen atom or a group eliminable under chromogenic development conditions, $R_1$ means a hydrogen or halogen atom, an optionally substituted alkyl, aryl or acylamino group, $R_2$ means an optionally substituted alkyl, aryl or heterocyclic group and n means a number from 0 to 3, is distinguished by improved stability of the cyan dye.

3 Claims, No Drawings

COLOR PHOTOGRAPHIC SILVER HALIDE MATERIAL

This invention relates to a colour photographic silver halide material having a novel polymeric cyan coupler.

Colour photographic recording materials which contain silver halide emulsions and so-called colour couplers for the formation of dyes are already known. The colour images arise from the reaction of the developer oxidation product with the colour couplers.

The most varied requirements are placed upon the colour couplers and the dyes formed therefrom. Colour couplers and dyes should generally be incorporated in a diffusion-resistant manner and the resultant dyes should exhibit good stability both in light and darkness, in particular on exposure to heat and moisture.

Cyan couplers are selected from three different classes depending upon the area of application:

a) 1-hydroxy-2-naphthamide compounds (for example U.S. Pat. No. 5,015,565).

The cyan dyes obtained therefrom exhibit absorption suitable for colour negative (CN) films (absorption maximum between 690 and 705 nm). Poor stability on storage in darkness and reduced dye yield in a spent bleaching bath are, however, disadvantageous.

b) 2-diacylaminophenols or 2-arylureido-5-acylaminophenols (for example U.S. Pat. Nos. 4,554,244, 3,880,661, 4,465,766).

The cyan dyes obtained therefrom are particularly suitable for CN films. As 2-equivalent couplers, they are highly reactive and provide a good colour yield even in a spent bleaching bath. The dyes exhibit an absorption maximum between 685 and 700 nm and very good resistance to moisture. Fading of the dyes, in particular at elevated temperatures, is, however, disadvantageous. The dyes moreover exhibit undesirable absorption in the green range of the spectrum.

c) 2-acylamino-5-alkylphenols (for example U.S. Pat. Nos. 3,772,002, 3,998,642).

These couplers, preferably having short-chain alkyl substituents, have favourable production costs and moreover exhibit good solubility in conventional coupler solvents. Coupler reactivity is very good, such that a good colour yield is obtained. The absorption maxima of the dyes are between 630 and 670 nm. They are thus preferably used in CN paper. However, very good stability on storage in darkness and elevated light stability of the dyes are required for this purpose. Exposure of the dyes to radiation may in particular result in considerable destruction of the image dye. This results in a change in the colour balance of the image, so impairing image quality. The colour balance also changes on storage in darkness as a result of destruction of the cyan dye. It is moreover necessary to use coupler solvents to introduce these couplers into the photographic material, which has a negative effect on layer thickness and sharpness.

It is known to use the colour couplers in the form of polymer dispersions, in which the functional residue of a colour coupler is linked once or more with a polymer backbone and is thus rendered diffusion-resistant. Such a polymer thus has repeating structural units containing the colour coupler.

Colour couplers which are incorporated in the layers of photographic recording materials in the form of such polymer dispersions are generally sufficiently resistant to diffusion and impair the mechanical properties of the layers only slightly even at low binder contents. It is particularly important that they do not crystallise during storage, exhibit good stability to light, heat and moisture and that the dyes produced therefrom are stable, exhibit the desired spectral characteristics and, on development, are precipitated non-diffusibly and as the finest possible grain. Colour couplers which are incorporated into photographic recording materials in the form of such polymer dispersions having a molecular weight of greater than 5000 generally exhibit good colloid stability and very adequately fulfil some of the requirements which are placed upon them.

Colour couplers of this type are described, for example, in U.S. Pat. No. 3,767,412, U.S. Pat. No. 4,804,620, U.S. Pat. No. 4,921,782, U.S. Pat. No. 4,946,771, U.S. Pat. No. 5,141,844, U.S. Pat. No. 5,151,356, EP 283 938, EP 316 955.

The use of phenolic monomers, for example in a free-radical polymerisation, is unfavourable since, as is known, phenols are free radical scavengers and thus have a negative influence on the chain growth of the polymer chains. A solution was thus sought for achieving satisfactory polymer quality.

The object of the invention is to provide novel, polymeric cyan couplers for use in colour materials, the image dyes of which exhibit elevated light stability. A further object of the invention is to improve the stability of these image dyes on storage in darkness and thus the colour reproduction of the corresponding colour material.

A third object of the invention is to improve the sharpness of the colour material. A fourth object is the provision of a polymeric cyan coupler which exhibits suitable molecular chain lengths and thus gives rise to more favourable stability values for the image dyes.

This object may be achieved with polymeric cyan couplers which contain a phenolic residue linked directly or via a short alkylene group with a polymer chain, position 4 of which phenolic residue is unsubstituted or substituted with an eliminable group.

The present invention accordingly provides a colour photographic silver halide material having a support and at least one photosensitive silver halide emulsion layer, characterised in that the silver halide material contains at least one polymeric cyan coupler associated with the photosensitive silver halide emulsion layer, which coupler contains polymerised units of the formula (I)

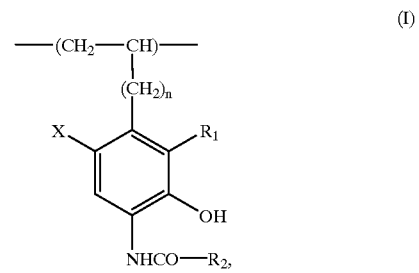

in which

X means a hydrogen atom or a group eliminable under chromogenic development conditions, $R_1$ means a hydrogen or halogen atom, an optionally substituted alkyl, aryl or acylamino group, $R_2$ means an optionally substituted alkyl, aryl or heterocyclic group and n means a number from 0 to 3.

Suitable monomers for the production of the polymer unit of the formula (I) are of the formula (II)

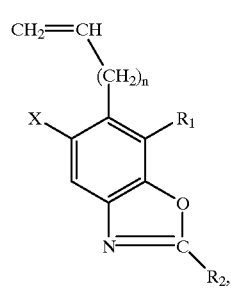
(II)

in which $R_1$, $R_2$, X and n have the above-stated meaning.

The compounds of the formula (II) are homopolymerised or copolymerised with at least one other comonomer and then subjected to alkaline cleavage to yield polymer units of the formula (I).

Preferably,

X means a hydrogen or chlorine atom, $R_1$ means a hydrogen, fluorine or chlorine atom or a methyl group, but in particular a chlorine atom and n means 0 or 1, in particular 0.

Suitable monomers of the formula (II) are:

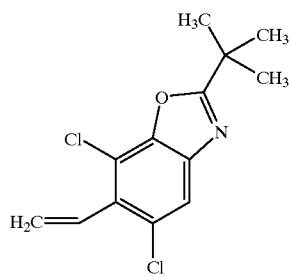
M-1

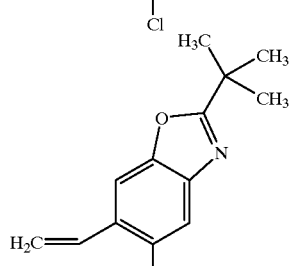
M-2

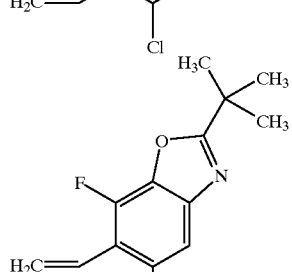
M-3

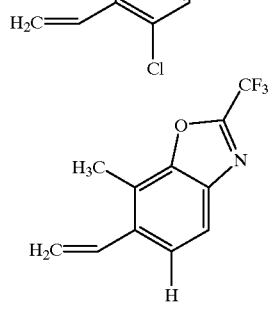
M-4

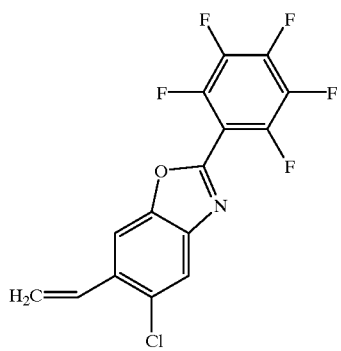
M-5

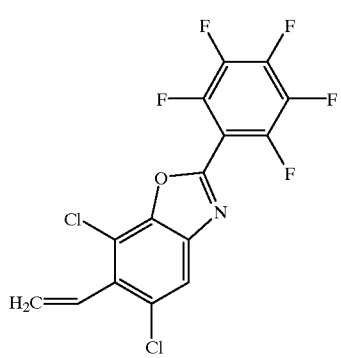
M-6

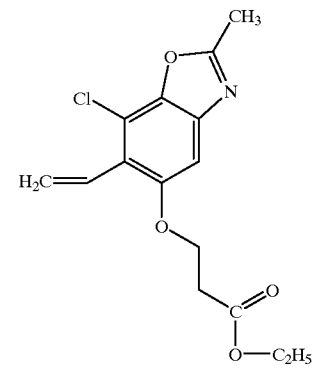
M-7

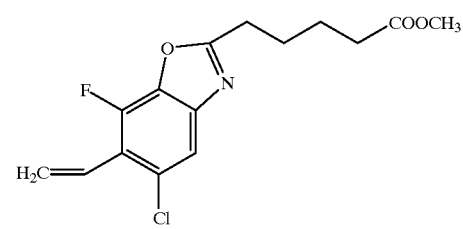
M-8

-continued
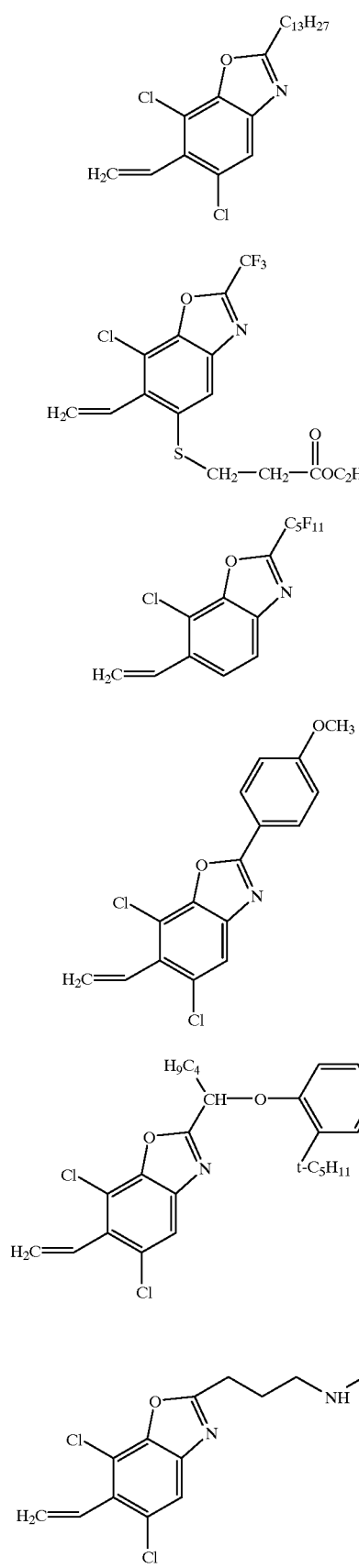

M-20
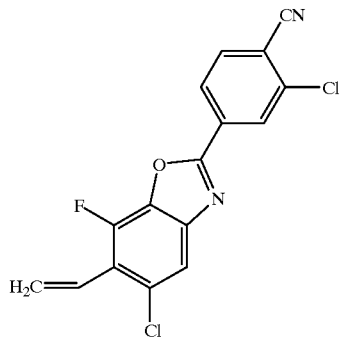
M-21
M-22
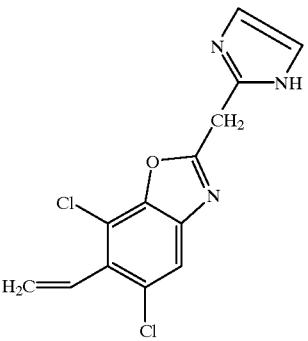
M-23
Production of the monomers is illustrated below by means of monomer M-1:
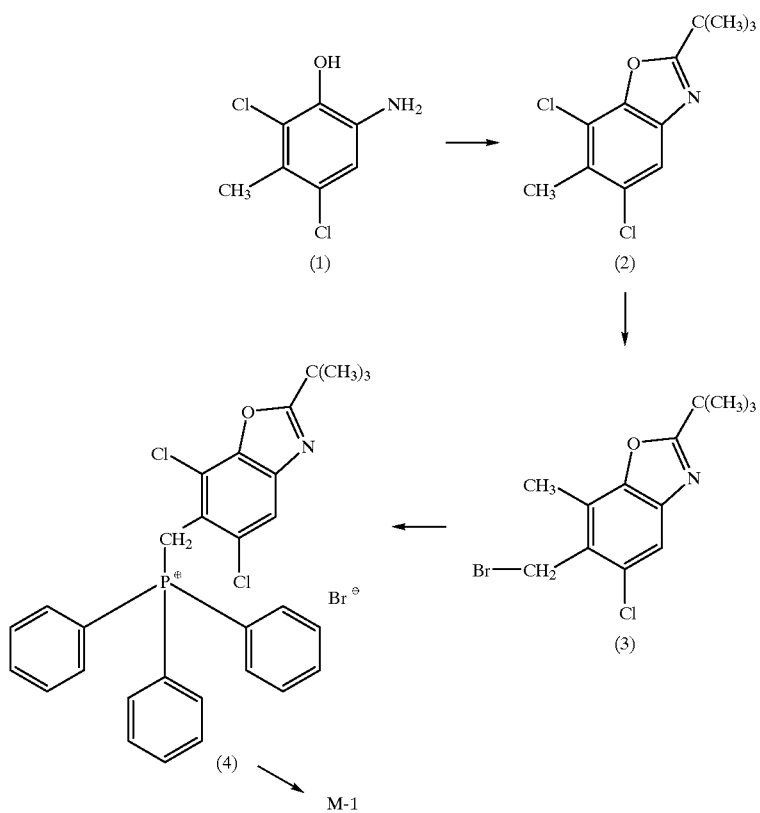

1.04 mol (200 g) of 2-amino-4,6-dichloro-5-methylphenol (1) were dissolved in 150 ml of dimethylacetamide. 1.09 mol (131 g) of 2,2-dimethylpropionic acid chloride were added dropwise at 50° C. Stirring was continued for 1 hour. The reaction solution was then combined with iced water. The organic constituents were extracted with 2.5 l of toluene. 0.93 mol (175 g) of p-toluenesulphonic acid hydrate were added to the organic phase and the mixture boiled for three hours with a water separator connected. After cooling, the reaction mixture was washed twice with water and the organic phase dried with $Na_2SO_4$. The solution was filtered and the solvent removed under a vacuum in a rotary evaporator. The residue was purified by recrystallisation from isopropanol. 173.2 g (64% of theoretical) of the oxazole (2) were obtained.

0.67 mol (173 g) of the oxazole (2) were dissolved in 1200 ml of $CCl_4$ and combined with 0.67 mol (119.3 g) of N-bromosuccinimide. After addition of 1 g of azobisisobutyronitrile, the solution was refluxed for three hours. Once the reaction was complete, succinimide was removed by suction filtration and the solvent removed under a vacuum in the rotary evaporator. 223.2 g (99% of theoretical) of the bromine compound (3) were obtained as a crude product.

0.64 mol (216 g) of the crude product (3) were then dissolved in 3.5 l of xylene and combined with 0.64 mol (167.8 g) of triphenylphosphine. The mixture was refluxed for three hours. A light-coloured precipitate is formed, which, once the reaction was complete, was removed by suction filtration, rewashed with ethyl acetate and dried. 349 g (91% of theoretical) of the phosphonium bromide (4) are obtained.

0.29 mol (174.5 g) of the phosphonium bromide (4) were suspended in 700 ml of 37 wt. % formaldehyde solution. 98 ml of 50 wt. % sodium hydroxide solution were added dropwise to the mixture and the mixture stirred for some hours. After standing overnight, the residue was filtered out, washed with water and dried. The residue was digested with diisopropyl ether. The insoluble constituents were then filtered out. The solvent was removed under a vacuum in the rotary evaporator and the residue purified by recrystallisation from methanol. 104.6 g (67% of theoretical) of M-1 having a melting point of 74° C. are obtained.

In addition to the starting monomers of the formula (II), further monomers may also be used for polymerisation, resulting in the formation of copolymers.

Examples of monomers (comonomers) are esters, preferably lower alkyl esters and amides, derived from an unsaturated acid, for example acrylic acid, α-chloroacrylic acid, methacrylic acid etc. (for example acrylamide, methyl methacrylate, ethyl acrylate, ethyl methacrylate, n-propyl acrylate, n-butyl acrylate, 2-ethylhexyl acrylate, n-hexyl acrylate, octyl methacrylate, lauryl methacrylate and methylene bisacrylamide etc.), vinyl esters (for example vinyl acetate, vinyl propionate and vinyl laurate etc.), acrylonitrile, methacrylonitrile, aromatic vinyl compounds (for example styrene and derivatives thereof, such as vinyltoluene, divinylbenzene, vinylacetophenone, sulphostyrene and styrenesulphonic acid etc.), itaconic acid, citraconic acid, crotonic acid, vinylidene chloride, vinyl alkyl ethers (for example vinyl ethyl ether etc.), esters of maleic acid, N-vinyl-2-pyrrolidone, N-vinyl-pyridine, 2- and 4-vinylpyridine, vinylimidazole, N-vinylacetamide, α-cyanoacrylic acid esters etc.

Esters of acrylic acid, of methacrylic acid and aromatic vinyl compounds are particularly preferred.

Two or more of the comonomer compounds described above may be used together. It is also possible, for example, to use a combination of n-butyl acrylate and divinylbenzene, styrene and methyl methacrylate, methyl acrylate and methacrylic acid etc.

The comonomer is selected such that it has a favourable influence upon the physical properties and/or chemical properties of the copolymer, for example improving solubility and compatibility with a binder such as gelatine in the photographic colloidal composition or other photographic additives, such as ultra-violet radiation absorbing agents, photographic anti-oxidants and colour couplers, together with flexibility and thermal stability.

In a preferred embodiment, the 20 to 60 wt. % of the comonomers are present in the polymeric cyan coupler.

The polymer latex according to the invention may be produced using an emulsion polymerisation process or by polymerising the monomers in an organic solvent and subsequently dispersing the solution in an aqueous solution of gelatine, or a water-soluble polymer may optionally be produced in the presence of emulsifiers.

These polymerisation methods may be used for the production of homopolymers and for the formation of copolymers. In the case of emulsion polymerisation, it is preferred that one comonomer is liquid as it acts as a solvent for the cyan coupler monomer, which is solid under normal conditions, during performance of the polymerisation.

Free-radical polymerisation of an ethylenically unsaturated monomer is initiated by thermal decomposition of a chemical initiator, by the action of a reducing agent on an oxidising compound (redox initiator) or by physical action, such as irradiation with ultra-violet radiation or other high-energy radiation, high frequencies etc.

Examples of chemical initiators are persulphate (for example ammonium per-sulphate or potassium persulphate etc.), hydrogen peroxide, peroxides (for example benzoyl peroxide or tert-butyl peroctoate etc.) and azonitrile compounds (for example 4,4'-azobis-(4-cyanovaleric acid) and azobisisobutyronitrile etc.).

Examples of conventional redox initiators are hydrogen peroxide/iron(II) salt, potassium persulphate/potassium bisulphite and cerium(IV) salt/alcohol etc.

Examples of the initiators and the functioning thereof are described by F. A. Bovey in *Emulsion Polymerization*, Interscience Publishers Inc., New York, 1955, pages 59 to 93.

Suitable emulsifiers are soaps, sulphonates, sulphates, cationic compounds, amphoteric compounds and protective colloids of an elevated molecular weight. Specific examples of the emulsions and the functioning thereof are described in *Belgische Chemische Industrie*, volume 28, pages 16 to 20, 1963.

The organic solvent which is used to dissolve the polymer may be removed from the mixture before casting when the polymer of the formula (I) is dispersed in an aqueous gelatine solution.

Solvents which may be considered are those which may readily be removed by rinsing, spray drying, vacuum or steam treatment.

Any type of dispersing agent may be used to disperse the polymeric coupler. Ionic surface-active agents and in particular anionic surface-active agents are, however, preferred.

It is furthermore possible to use ampholytic surface-active agents, such as C-cetylbetaine, an N-alkylamino propionate and an N-alkylimino dipropionate etc.

The molecular weights of the coupler polymers according to the invention are inter alia greater than 5000, preferably greater than 20000, in order to ensure sufficient diffusion-resistance. The upper limit is not critical and, especially if di- or polyfunctional monomers are used as a comonomer, may reach values of above 10 million.

Examples of colour photographic materials are colour negative films, colour reversal films, colour positive films, colour photographic paper, colour reversal photographic paper, colour-sensitive materials for the dye diffusion transfer process or the silver dye bleaching process. A review is given in *Research Disclosure* 37038 (1995) and *Research Disclosure* 38957 (1996).

The photographic materials consist of a support onto which at least one photosensitive silver halide emulsion layer is applied. Thin films and sheets are in particular suitable as supports. A review of support materials and the auxiliary layers applied to the front and reverse sides of which is given in *Research Disclosure* 37254, part 1 (1995), page 285 and in *Research Disclosure* 38957, part XV (1996), page 627.

The colour photographic materials conventionally contain at least one red-sensitive, one green-sensitive and one blue-sensitive silver halide emulsion layer, optionally together with interlayers and protective layers.

Depending upon the type of the photographic material, these layers may be differently arranged. This is demonstrated for the most important products:

Colour photographic films such as colour negative films and colour reversal films have on the support, in the stated sequence, 2 or 3 red-sensitive, cyan-coupling silver halide emulsion layers, 2 or 3 green-sensitive, magenta-coupling silver halide emulsion layers and 2 or 3 blue-sensitive, yellow-coupling silver halide emulsion layers. The layers of identical spectral sensitivity differ with regard to their photographic sensitivity, wherein the less sensitive sub-layers are generally arranged closer to the support than the more highly sensitive sub-layers.

A yellow filter layer, which prevents blue light from reaching the underlying layers, is conventionally located between the green-sensitive and blue-sensitive layers.

Possible options for different layer arrangements and the effects thereof on photographic properties are described in *J. Inf. Rec. Mats.*, 1994, volume 22, pages 183–193 and in *Research Disclosure* 38957, part XI (1996), page 624.

Colour photographic paper, which is usually substantially less photosensitive than a colour photographic film, conventionally has on the support, in the stated sequence, one blue-sensitive, yellow-coupling silver halide emulsion layer, one green-sensitive, magenta-coupling silver halide emulsion layer and one red-sensitive, cyan-coupling silver halide emulsion layer; the yellow filter layer may be omitted.

The number and arrangement of the photosensitive layers may be varied in order to achieve specific results. For example, all high sensitivity layers may be grouped together in one package of layers and all low sensitivity layers may be grouped together in another package of layers in order to increase sensitivity (DE-25 30 645).

The substantial constituents of the photographic emulsion layers are binder, silver halide grains and colour couplers.

Details of suitable binders may be found in *Research Disclosure* 37254, part 2 (1995), page 286 and in *Research Disclosure* 38957, part II.A (1996), page 598.

Details of suitable silver halide emulsions, the production, ripening, stabilisation and spectral sensitisation thereof, including suitable spectral sensitisers, may be found in *Research Disclosure* 37254, part 3 (1995), page 286 and in *Research Disclosure* 37038, part XV (1995), pace 89 and in *Research Disclosure* 38957, part V.A (1996), page 603.

Photographic materials with camera sensitivity conventionally contain silver bromide-iodide emulsions, which may optionally also contain small proportions of silver chloride. Photographic print materials contain either silver chloride-bromide emulsions with up to 80 wt. % of AgBr or silver chloride-bromide emulsions with above 95 mol. % of AgCl.

Details relating to colour couplers may be found in *Research Disclosure* 37254, part 4 (1995), page 288, in *Research Disclosure* 37038, part II (1995), page 80 and in *Research Disclosure* 38957, part X.B (1996), page 616. The maximum absorption of the dyes formed from the couplers and the developer oxidation product is preferably within the following ranges: yellow coupler 430 to 460 nm, magenta coupler 540 to 560 nm, cyan coupler 630 to 700 nm.

In order to improve sensitivity, grain, sharpness and colour separation in colour photographic films, compounds are frequently used which, on reaction with the developer oxidation product, release photographically active compounds, for example DIR couplers which eliminate a development inhibitor.

Details relating to such compounds, in particular couplers, may be found in *Research Disclosure* 37254, part 5 (1995), page 290, in *Research Disclosure* 37038, part XIV (1995), page 86 and in *Research Disclosure* 38957, part X.C (1996), page 618.

Colour couplers, which are usually hydrophobic, as well as other hydrophobic constituents of the layers, are conventionally dissolved or dispersed in high-boiling organic solvents. These solutions or dispersions are then emulsified into an aqueous binder solution (conventionally a gelatine solution) and, once the layers have dried, are present in the layers as fine droplets (0.05 to 0.8 μm in diameter).

Suitable high-boiling organic solvents, methods for the introduction thereof into the layers of a photographic material and further methods for introducing chemical compounds into photographic layers may be found in *Research Disclosure* 37254, part 6 (1995), page 292.

The non-photosensitive interlayers generally located between layers of different spectral sensitivity may contain agents which prevent an undesirable diffusion of developer oxidation products from one photosensitive layer into another photo-sensitive layer with a different spectral sensitisation.

Suitable compounds (white couplers, scavengers or DOP scavengers) may be found in *Research Disclosure* 37254, part 7 (1995), page 292, in *Research Disclosure* 37038, part III (1995), page 84 and in *Research Disclosure* 38957, part X.D (1996), pages 621 et seq.

The photographic material may also contain UV light absorbing compounds, optical brighteners, spacers, filter dyes, formalin scavengers, light stabilisers, anti-oxidants, $D_{min}$ dyes, plasticisers (latices), biocides and additives to improve the stability of dyes and couplers, to reduce colour fogging and to reduce yellowing and others. Suitable compounds may be found in *Research Disclosure* 37254, part 8 (1995), page 292, in *Research Disclosure* 37038, parts IV, V, VI, VII, X, XI and XIII (1995), pages 84 et seq. and in *Research Disclosure* 38957, parts VI, VIII, IX and X (1996), pages 607 and 610 et seq.

The layers of colour photographic materials are conventionally hardened, i.e. the binder used, preferably gelatine, is crosslinked by appropriate chemical methods.

Suitable hardener substances may be found in *Research Disclosure* 37254, part 9 (1995), page 294, in *Research Disclosure* 37038, part XII (1995), page 86 and in *Research Disclosure* 38957, part II.B (1996), page 599.

Once exposed with an image, colour photographic materials are processed using different processes depending upon their nature. Details relating to processing methods and the necessary chemicals are disclosed in *Research Disclosure* 37254, part 10 (1995), page 294, in *Research Disclosure* 37038, parts XVI to XXIII (1995), pages 95 et seq. and in *Research Disclosure* 38957, parts XVIII, XIX and XX (1996), pages 630 et seq. together with example materials.

Production of Particularly Preferred Polymers
Production Example, polymer P 1

66 ml of water and 0.66 g (5 wt. %) of oleoylmethyltauride Na salt are heated to 80° C. under nitrogen. 3.96 g of M-1 and 9 ml of methanol are then stirred in in this order. 8.58 g of methyl acrylate, 0.66 g of trivinylcyclohexane, dissolved in 7.6 ml of methanol, and 26.4 g of 1 wt. % aqueous potassium peroxydisulphate solution are then apportioned within one hour. Stirring is performed for two hours at 80° C. The mixture is filtered while hot and the methanol removed under a vacuum. Determination of content after filtration reveals a solids content of 14.7 wt. % (yield 98% of theoretical).

Cleavage of oxazole ring 40 g of the polymer latex obtained above are heated to boiling point with 29.8 g of 10 wt. % potassium hydroxide solution. After 5 minutes, the pH is 13.3. After 4.5 hours' stirring, the pH has fallen to 12.9. The pH is adjusted to 7 with dilute HCl solution and the solution dialysed for several hours. The solvent is thereupon reduced to a volume of 75 ml. Yield is 95% of theoretical. The polymer couplers are put to further use in the form of the resultant latex. The average particle size of the resultant latex is approx. 120 nm.

A similar method is used for the production of polymers P 2 to P 15, wherein the nature and weight ratio of the monomers was modified.

TABLE 1

| Polymer | Monomer | wt. % | Comonomers (wt. %) | Comonomers having acid groups after hydrolysis (wt. %) |
|---|---|---|---|---|
| P 1 | M-1 | 30 | Methyl acrylate (65) Trivinylcyclohexane (5) | 45 |
| P 2 | M-1 | 50 | Methyl acrylate (45) Trivinylcyclohexane (5) | 60 |
| P 3 | M-1 | 50 | Methyl methacrylate (50) | 62 |
| P 4 | M-1 | 35 | Butyl methacrylate (65) Trivinylcyclohexane (5) | 43 |
| P 5 | M-1 | 45 | Styrene (55) | 45 |
| P 6 | M-1 | 35 | i-Propyl acrylate (55) 4-Vinylpyridine (10) | 54 |
| P 7 | M-2 | 35 | Styrene (55) Divinylbenzene (10) | 34 |
| P 8 | M-2 | 35 | Hydroyethyl acrylate (40) Butyl acrylate (25) | 40 |
| P 9 | M-2 | 50 | Methyl methacrylate (40) Hydroxyethyl acrylate (10) | 59 |
| P 10 | M-2 | 40 | 2-Ethyhexyl acrylate (55) Divinylbenzene (5) | 43 |
| P 11 | M-3 | 40 | Styrene (50) i-Propyl acrylate (10) | 42 |
| P 12 | M-3 | 50 | Butyl methacrylate (50) | 61 |
| P 13 | M-3 | 40 | i-Propyl acrylate (55) Ethylene glycol dimethacrylate (5) | 49 |
| P 14 | M-3 | 40 | Styrene (40) 4-Vinylpyridine (20) | 40 |
| P 15 | M-3 | 35 | Butyl acrylate (50) 4-Vinylpyridine (15) | 44 |

EXAMPLE 1

Example 1

A colour photographic recording material suitable for a rapid processing process was produced by applying the following layers in the stated sequence onto a film base made from paper coated on both sides with polyethylene. Quantities are all stated per 1 $m^2$. The silver halide application rate is stated as the corresponding quantities of $AgNO_3$.

Sample 1

Layer 1: (Substrate layer)
　0.20 g of gelatine
Layer 2: (Blue-sensitive layer)
　Blue-sensitive silver halide emulsion (99.5 mol. % chloride,
　0.5 mol. % bromide, average grain diameter 0.8 μm, prepared from
　0.5 g of $AgNO_3$ with
　　1.38 g of gelatine
　　0.60 g of yellow coupler Y-1
　　0.29 g of oil former OF-1
　　0.15 g of dye stabiliser ST-1
Layer 3: (Interlayer)
　1.10 g of gelatine
　0.04 g of 2,5-di-tert.-octylhydroquinone
　0.04 g of tricresyl phosphate (TCP)
　0.04 g of compound SC-1
Layer 4: (Green-sensitive layer)
　Green-sensitised silver halide emulsion (99.5 mol. % chloride,
　0.5 mol. % bromide, average grain diameter 0.45 μm) prepared from
　0.30 g of $AgNO_3$ with
　　1.08 g of gelatine
　　0.44 g of magenta coupler M-1
　　0.15 g of dye stabiliser ST-2
　　0.31 g of dibutyl adipate (DBA)
　　0.10 g of tetradecanol
Layer 5: (UV protective layer)
　1.15 g of gelatine
　0.40 g of UV absorber UV-1
　0.20 g of UV absorber UV-2
　0.025 g of 2,5-dioctylhydroquinone
　0.02 g of compound SC-1
　0.20 g of oil former OF-2
　0.04 g of TCP
Layer 6: (Red-sensitive layer)
　Red-sensitised silver halide emulsion (99.5 mol. % chloride,
　0.5 mol. % bromide, average grain diameter 0.5 μm) prepared from
　0.30 g of $AgNO_3$ with
　　0.75 g of gelatine
　　0.36 g of cyan coupler C-1
　　0.36 g of TCP
Layer 7: (UV protective layer)
　0.35 g of gelatine
　0.15 g of UV absorber UV-1
　0.05 g of UV absorber UV-2
　0.15 g of oil former OF-2
Layer 8: (Protective layer)
　0.90 g of gelatine
　0.30 g of hardener H-1

The following compounds were used in sample 1:

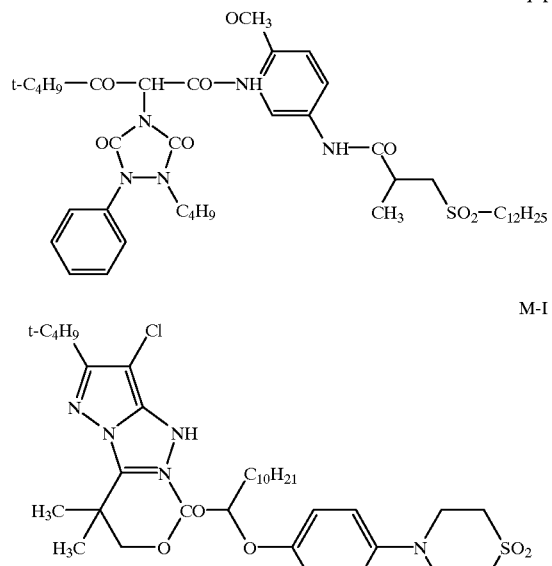

Y-I

M-I

C-I

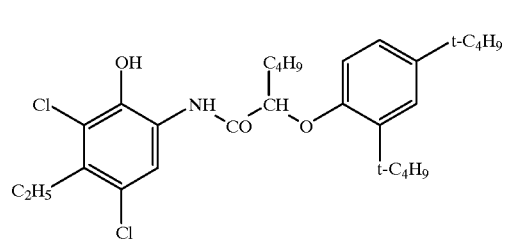

ST-1

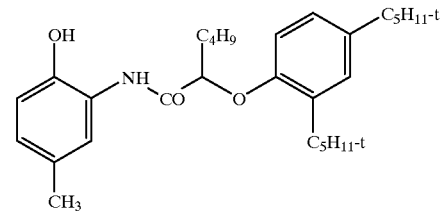

ST-2

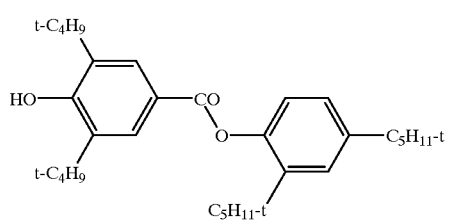

SC-1

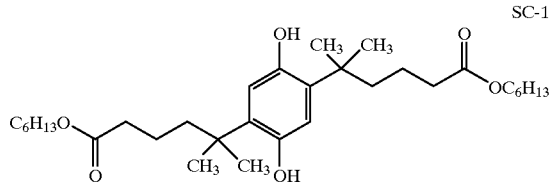

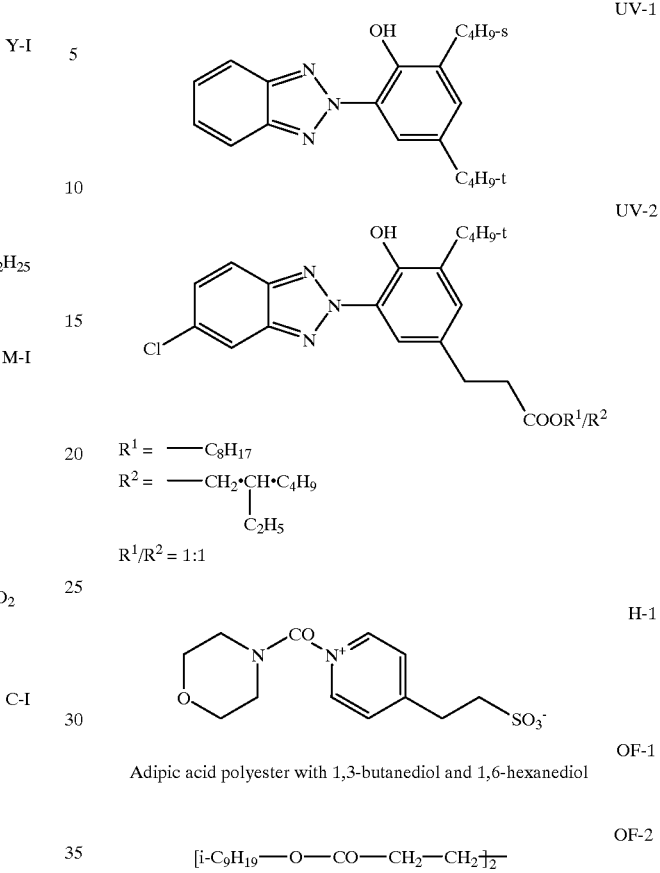

UV-1

UV-2

$R^1 = \text{—} C_8H_{17}$
$R^2 = \text{—} CH_2\text{·}CH\text{·}C_4H_9$
           $|$
           $C_2H_5$ $R^1/R^2 = 1:1$

H-1

OF-1

Adipic acid polyester with 1,3-butanediol and 1,6-hexanediol

OF-2

$[\text{i-}C_9H_{19}\text{—}O\text{—}CO\text{—}CH_2\text{—}CH_2]_{\overline{2}}$ Samples 2 to 6

As sample 1, but instead of C-1 in layer 6, equimolar quantities (relative to the chromogenic group) of the polymer couplers stated in table 2 are used. The polymer latices are added to the casting solution as 6 wt. % aqueous solutions.

The gelatine content of samples 1 to 6 is identical.

The samples were then exposed behind a graduated grey wedge and processed as follows:

| a) | Colour developer - 45 s - 35° C. | |
|---|---|---|
| | Triethanolamine | 9.0 g |
| | N,N-diethylhydroxylamine | 4.0 g |
| | Diethylene glycol | 0.05 g |
| | 3-methyl-4-amino-N-ethyl-N-methanesulphonamido-ethylaniline sulphate | 5.0 g |
| | Potassium sulphite | 0.2 g |
| | Triethylene glycol | 0.05 g |
| | Potassium carbonate | 22 g |
| | Potassium hydroxide | 0.4 g |
| | Ethylenediaminetetraacetic acid, disodium salt | 2.2 g |
| | Potassium chloride | 2.5 g |
| | 1,2-dihydroxybenzene-3,4,6-trisulphonic acid, trisodium salt | 0.3 g |
| | make up to 1000 ml with water, pH 10.0 | |

| b) | Bleach/fixing bath - 45 s - 35° C. | |
|---|---|---|
| | Ammonium thiosulphate | 75 g |
| | Sodium hydrogen sulphite | 13.5 g |
| | Ammonium acetate | 2.0 g |
| | Ethylenediaminetetraacetic acid (iron/ammonium salt) | 57 g |
| | make up to 1000 ml with water | |
| | adjust pH to 5.5 with Ammonia, 25% by weight or acetic acid | 9.5 g |
| c) | Rinsing - 2 min - 33° C. | |
| d) | Drying | |

Cyan gradation and cyan maximum density were then measured (table 2).

The samples were then stored in darkness for 84 days at 80° C., 50% relative humidity and the percentage loss in cyan maximum density determined (table 2).

TABLE 2

| Sample | Coupler | Polymer | Monomer | Cyan gradation | $D_{max}$ | Δ density (storage in darkness) |
|---|---|---|---|---|---|---|
| 1 | C-1 | | | 295 | 239 | −32 |
| 2 | | P 1 | M-1 | 305 | 250 | −25 |
| 3 | | P 2 | M-1 | 307 | 253 | −20 |
| 4 | | P 3 | M-1 | 300 | 245 | −25 |
| 5 | | P 4 | M-1 | 301 | 241 | −21 |
| 6 | | P 5 | M-1 | 310 | 249 | −20 |

Example 2

Sample 7

As Example 1, sample 1, but, instead of magenta coupler M-1, 0.38 g of M-2 are used in layer 4

M-2

(structure of M-2: pyrazolotriazole with (CH$_3$)$_3$C, Cl substituents, linked via phenyl-NH-CO-CH$_2$-CH$_2$-C(O)-O-C$_{14}$H$_{29}$)

and, instead of cyan coupler C-1, 0.34 g of C-2 are used in layer 6:

C-2

(structure of C-2: phenol with OH, Cl, CH$_3$, Cl substituents and NH-C(O)-C$_{13}$H$_{27}$)

Samples 8 to 12

As sample 7, but, instead of C-2, equimolar quantities of polymeric couplers according to table 3 are added. The couplers are introduced as in samples 2 to 6. Cyan gradation and cyan maximum density were measured (table 3).

TABLE 3

| Sample | Coupler | Polymer | Monomer | Cyan gradation | $D_{max}$ | Δ density (storage in darkness) |
|---|---|---|---|---|---|---|
| 7 | C-2 | | | 280 | 232 | −45 |
| 8 | | P 6 | M-1 | 299 | 248 | −26 |
| 9 | | P 7 | M-2 | 297 | 245 | −19 |
| 10 | | P 8 | M-2 | 305 | 251 | −24 |
| 11 | | P 9 | M-2 | 302 | 247 | −23 |
| 12 | | P 10 | M-2 | 299 | 243 | −22 |

Example 4

Sample 13

As sample 1, but, instead of magenta coupler M-1, 0.40 g of M-3 are used in layer 4:

M-3

(structure of M-3: pyrazolotriazole with H$_3$C, Cl substituents, linked via CH(CH$_3$)-CH$_2$-NHC(O)-CH(C$_6$H$_{13}$(n))-O-phenyl with t-C$_5$H$_{11}$ groups)

and, instead of cyan coupler C-1, 0.53 g of C-3 are used in layer 6:

C-3

(structure of C-3: phenol with OH, Cl, CH$_3$, Cl substituents and NH-C(O)-C$_{13}$H$_{27}$)

Samples 14 to 18

As sample 13, but, instead of C-3, equimolar quantities of polymeric couplers ng to table 4 are added. The couplers are introduced as in samples 2 to 6.

TABLE 4

| Sample | Coupler | Polymer | Monomer | Cyan gradation | $D_{max}$ | Δ density (storage in darkness) |
|---|---|---|---|---|---|---|
| 13 | C-3 | | | 294 | 237 | −35 |
| 14 | | P 11 | M-3 | 297 | 243 | −29 |
| 15 | | P 12 | M-3 | 301 | 238 | −25 |
| 16 | | P 13 | M-3 | 305 | 252 | −28 |
| 17 | | P 14 | M-3 | 298 | 246 | −22 |
| 18 | | P 15 | M-3 | 307 | 240 | −24 |

As is evident from tables 2 to 4, storage stability in darkness is substantially improved in materials containing the polymeric couplers according to the invention in comparison with materials containing conventional couplers. Moreover, properties such as maximum density and gradation are also better than in the comparison materials.

Example 4

The exposed and processed samples 1 to 6 were exposed to 20×10$^6$ Lux h of light from a daylight-standardised xenon lamp. The percentage decrease in density was then measured (table 5).

TABLE 5

| | | | | Percentage decrease in density at initial density | | |
|---|---|---|---|---|---|---|
| Sample | Coupler | Polymer | Monomer | D = 0.6 | D = 1.0 | D = 1.4 |
| 1 | C-1 | | | 55 | 48 | 40 |
| 2 | | P 1 | M-1 | 37 | 30 | 27 |
| 3 | | P 2 | M-1 | 40 | 31 | 29 |
| 4 | | P 3 | M-1 | 39 | 32 | 30 |
| 5 | | P 4 | M-1 | 36 | 30 | 29 |
| 6 | | P 5 | M-1 | 34 | 29 | 27 |

It is evident from table 5 that the light stability of the materials containing a polymeric coupler according to the invention is substantially better than the light stability of the comparison material. This applies to all density ranges.

What is claimed is:

1. A color photographic silver halide material which comprises at least one photosensitive silver halide emulsion layer, and at least one polymeric cyan coupler associated with the photosensitive silver halide emulsion layer, which coupler contains polymerized units of the formula (I)

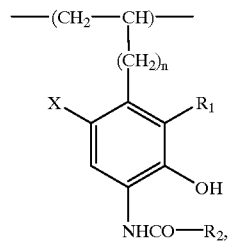

in which
  X is a hydrogen atom or a group eliminable under chromogenic development conditions,
  $R_1$ is a hydrogen or halogen atom, an optionally substituted alkyl, aryl or acylamino group,
  $R_2$ is an optionally substituted alkyl, aryl or heterocyclic group and
  n is a number from 0 to 3.

2. The color photographic silver halide material according to claim 1, wherein
  X is a hydrogen or chlorine atom
  $R_1$ is hydrogen, fluorine atom, chlorine atom or a methyl group and
  n is 0 or 1.

3. The color photographic silver halide material according to claim 2, wherein $R_1$ is a chlorine atom and n is 0.

* * * * *